United States Patent

Desai et al.

[11] Patent Number: 5,858,930
[45] Date of Patent: Jan. 12, 1999

[54] LIQUID BENZ-ISO-QUINOLINE DERIVATIVES

[75] Inventors: Bharat Desai, Ringwood, N.J.; Michael J. Smith, Newtown, Pa.

[73] Assignee: United Color Manufacturing, Inc., Newtown, Pa.

[21] Appl. No.: 866,032

[22] Filed: May 30, 1997

[51] Int. Cl.⁶ ........................ C10M 133/40; C09K 5/00
[52] U.S. Cl. ........................ 508/261; 508/266; 252/68; 546/100
[58] Field of Search ................... 508/261, 266; 546/100

[56] References Cited

U.S. PATENT DOCUMENTS

| | | | |
|---|---|---|---|
| Re. 35,370 | 11/1996 | Henry | 73/40.7 |
| Re. 35,395 | 12/1996 | Henry | 73/40.7 |
| 2,006,017 | 6/1935 | Eckert et al. | 260/124 |
| 2,385,106 | 9/1945 | Scalera et al. | 260/281 |
| 2,415,373 | 2/1947 | Scalera et al. | 546/100 |
| 2,715,126 | 8/1955 | Mulvaney et al. | 546/100 |
| 2,914,531 | 11/1959 | Staeuble et al. | 546/100 |
| 3,310,564 | 3/1967 | Kasai | 546/100 |
| 3,935,227 | 1/1976 | Wade et al. | 546/100 |
| 4,040,968 | 8/1977 | Harris | 508/261 |
| 4,115,555 | 9/1978 | Wade et al. | 546/100 |
| 4,200,752 | 4/1980 | Bertelson | 546/100 |
| 4,575,480 | 3/1986 | Kotani et al. | 430/192 |
| 4,758,366 | 7/1988 | Parekh | 252/68 |
| 5,149,453 | 9/1992 | Parekh | 252/68 |
| 5,202,318 | 4/1993 | Berger et al. | 546/100 |
| 5,235,045 | 8/1993 | Lewis et al. | 534/560 |
| 5,279,967 | 1/1994 | Bode | 436/56 |
| 5,308,773 | 5/1994 | Lewis et al. | 436/73 |
| 5,420,136 | 5/1995 | Lewis et al. | 514/296 |

OTHER PUBLICATIONS

EPA Premanufacture Notice for New Chemical Substances, EPA No. PMN 84–570, Document control 51–8400570, 1984 (no month).

*Primary Examiner*—Ellen M. McAvoy
*Attorney, Agent, or Firm*—Howrey & Simon

[57] ABSTRACT

1,8-Naphthalimide derivatives of Formula (I) are useful as fluorescent dyes:

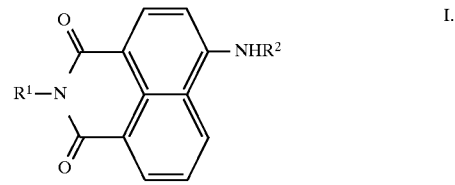

wherein $R^1$ and $R^2$ are each independently selected from the group consisting of branched alkyl groups containing 7–8 carbon atoms and alkyloxyalkyl groups containing 4 to 24 carbon atoms.

31 Claims, No Drawings

LIQUID BENZ-ISO-QUINOLINE DERIVATIVES

BACKGROUND OF THE INVENTION

1. Field of the Invention

The present invention relates to alkylamino/imino Benz-iso-Quinoline derivatives that are useful as fluorescent leak detection dyes in lubricants.

2. Description of the Related Art

Derivatives of 1H-Benz(de)isoquinoline-1,3(2H)-diones, sometimes named as 1,8-naphthalimides, have been known for some time (See for example U.S. Pat. Nos. 2,006,017 and 2,385,106) and are mainly utilized either as optical brightening agents or bright fluorescent yellow dyes applied to natural and man-made textile fibers. In all these applications the compounds are required to possess some degree of water solubility. Water-insoluble compounds have also been proposed as fluorescent dyes for certain thermoplastics, for example, polystyrene and for imparting fluorescent effects to petroleum hydrocarbon based fuels and lubricants, either for aesthetic reasons or for detecting leakage of fluid. An example of the latter usage is described in U.S. Pat. No. 4,758,366. When a leak occurs, the dye present in the lubricant composition is deposited on the area of the container surrounding the leak. Upon exposure to long wave ultraviolet light, also called "black light", the dye fluoresces. By irradiating the exterior of the container, a leak and its location can be visually determined by the fluorescent response. Such a method is generally convenient for determining the presence and location of small leaks.

This type of method has become especially valuable in detecting refrigerant fluid leaks from automobile, domestic, and industrial air conditioning and refrigeration systems, since such a leak implies the loss of halogenated refrigerant gas. Escape of these types of gases is of primary environmental concern due to the possible damage they do to the ultraviolet light absorbing ozone gas layer of the earth's upper atmosphere. The dye which has almost entirely dominated this technique in commercial practice is N-butyl-4-butylamino-1,8-naphthalimide, a compound named by Chemical Abstracts Services as 1H-Benz[de]isoquinoline-1,3(2H)dione, 2-butyl-6-(butylamino) and identified by the "Colour Index" system of classification as C.I. Solvent Yellow 43 (hereinafter referred to as "Solvent Yellow 43"). This compound is a dry powder dye with a melting point of 127° C. It has a comparatively low direct solubility, not exceeding 1% in contemporary hydrocarbon based refrigerant oils, and less in the more recently developed refrigerant lubricants such as polyalkylene glycols and their esters. Because of its low direct solubility in the refrigerant oils, and the inconvenience of handling dry powder dye in an engineering plant, Solvent Yellow 43 is normally supplied as a pourable, but viscous, concentrate solution that contains up to 20% by weight of the dye in an organic solvent such as aromatic hydrocarbons. These concentrates are relatively clean to handle and can be diluted directly into the refrigerant oils.

However, the development of new lubricants, which are adapted to be miscible with the now required non-CFC refrigerants, has caused a problem with the use of Solvent Yellow 43. Specifically, Solvent Yellow 43 tends to crystallize out of these lubricant compositions during use. The precipitated crystals can clog various portions of the refrigeration equipment, such as the fine jets, thereby causing a shut down of the system. Accordingly, Solvent Yellow 43 is not practically employed in the new type of refrigerant lubricants.

Another dye proposed for leak detection in refrigerant compositions is apparently N-(iso)nonyl4-(iso)nonylamino-1,8-naphthalimide. This dye, like Solvent Yellow 43, is quite acceptable when used with conventional lubricants such as mineral oil, but, is problematic when used in the newer types of lubricants. The dye can precipitate out as a tarry mass during use due to the absorption of small amounts of water by the refrigerant lubricant, especially those based on the newer polyalkylene glycol ester type oil. Consequently, this dye is not a practical alternative to Solvent Yellow 43 in the newer refrigerant lubricants.

Accordingly, there is a demand for a fluorescent dye that is compatible with a wide variety of lubricant compositions and oils and which will not crystallize or otherwise fall out of solution over a wide range of operating temperatures, durations, and conditions. The present invention provides fluorescent dye compounds and lubricant compositions for a refrigerant that enables fluorescent leak detection. Fluorescent dyes of the present invention, moreover, do not require aromatic hydrocarbons or other cosolvents in order to be incorporated into a lubricant composition.

SUMMARY OF THE INVENTION

The present invention provides compounds of formula (I):

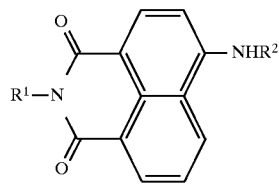

wherein $R^1$ and $R^2$ are each independently selected from branched alkyl groups containing 7 to 8 carbon atoms and alkyloxyalkyl groups containing 4 to 24 carbon atoms.

DETAILED DESCRIPTION OF THE INVENTION

In accordance with the present invention, by careful selection of the substituents $R^1$ and $R^2$ of the 1,8-naphthalimide ring structure, a dye can be obtained that has excellent stability in lubricant compositions under a refrigeration cycle environment while simultaneously providing sufficient fluorescent efficiency. $R^1$ and $R^2$ are "independently selected," meaning that they may be the same or different. The substituent groups represented by $R^1$ and $R^2$ are a branched alkyl group containing 7 or 8 carbon atoms or an alkyloxyalkyl group containing 4 to 24 carbon atoms. The branched alkyl groups include single and multiple branching. Typical branched alkyl groups include 2-ethylhexyl, 2-methylhexyl, 2-methylheptyl, 1-ethylhexyl, 1-methylhexyl, 1-methylheptyl, 4-ethylhexyl, 2,5-dimethylhexyl and the like. The alkyloxyalkyl group preferably contains in the alkyloxy moiety 1–15 carbon atoms, more preferably 6–10 carbon atoms. The alkyl moiety of the alkyloxyalkyl group preferably contains 2–8 carbon atoms, more preferably 3 carbon atoms. For clarity, the "alkyloxy moiety" is the terminal portion of the alkyloxyalkyl group and the "alkyl moiety" is the divalent connector between the nitrogen atom and the oxygen atom (of the alkyloxy group). The alkyl groups in the alkyloxy moiety can be branched or straight chain. The alkyloxyalkyl groups may contain repeating groups, i.e., multiple ether linkages. Typical examples of alkyloxyalkyl groups include 2-ethylhexyloxypropyl, tridecyloxypropyl, methyloxypropyl, propyloxypropyl, 4-ethylhexyloxyethyl, methyloxyhexyloxypropyl and the like.

The compounds of formula (I) are liquid, meaning that the compound is in the liquid state at room temperature and atmospheric pressure. Preferred compounds exhibit a melting or setting point at −5° F. or less. The compounds are typically very viscous. As a liquid, the dyes can be directly handled and added to the lubricant composition without the need to first dissolve the dye into a carrier solvent. The liquid dye is generally fully miscible with lubricant compositions, even in high amounts. This liquid nature of the dye also permits the dilution thereof, if desired, to form a more conveniently pourable viscosity by the addition of only a minimal amount of appropriate solvent(s). Indeed, the preferred compounds of the invention can be directly combined (as a reaction product) with such an appropriate solvent without the need for additional processing.

By contrast, Solvent Yellow 43 has to be isolated by filtration, dried, and then pulverized before combining with a solvent to form the liquid concentrate. The drying, grinding, and handling of the dusty, powdered dye is inconvenient, time consuming and environmentally undesirable. The preferred compounds of the present invention do not suffer from these additional processing steps and are thus more expeditious and environmentally friendly to handle than Solvent Yellow 43.

The compounds of formula (I) can be synthesized by well-documented methods from conventional, readily available or derivable starting materials by a worker skilled in this art without undue experimentation. Typically the synthesis involves the condensation of an alkyl or an alkylether primary amine with a naphthalic acid or naphthalic anhydride substituted in the 4 (or 5) position by a grouping replaceable by the amine. Suitable groupings include nitro or sulfonic acid groupings or chlorine or bromine atoms. The latter is particularly preferred due to its comparatively high reactivity and ready availability. The compounds of formula (I) may also be prepared, somewhat less conveniently, by the reductive alkylation of 4 nitronaphthalic acid or anhydride preceded or followed by formation of the imide ring. The reactions may be carried out either under aqueous or non-aqueous conditions as circumstances dictate and at conventional temperatures and conditions.

The compounds of formula (I) can be used in various oil and lubricant compositions as a dye for identification purposes, aesthetic reasons, or leak detection. Preferably the dye is used in a refrigerant lubricant. This includes the conventional refrigerant lubricants based on mineral oils or other hydrocarbon compounds as well as the new refrigerant lubricants. The term "new refrigerant lubricants" refers to the lubricant compositions formulated to accommodate non-chlorine-containing refrigerants. Preferably the new refrigerant lubricants are "R-134a lubricants", meaning that the refrigerant R-134a (1,1,1,2-tetrafluoroethane) is fully miscible and compatible (no phase separation) with the lubricant over a temperature range of from −20° C. to 50° C. at essentially all mixing ratios, such as from 1/99 to 99/1.

The refrigerant lubricant is comprised mainly or solely of natural and/or synthetic oils. The oils include naphthalenic oils such as alkyl naphthalenes; paraffinic oils; alkylated benzene oils; polyalkyl silicate oils; polyglycols such as polyalkylene glycols, polyoxyalkylene glycols and etherfied or polyol adducts thereof; esters such as polyol esters, dibasic acid esters, and polyesters; polyether polyols; polyvinyl ethers, polycarbonates; fluorinated silicones such as fluorinated polysiloxanes; perfluoroethers; and aromatic compounds with fluoroalkyloxy or fluoroalkylthio substituents. These oils are described in the following U.S. Pat. Nos. and in the references cited therein: 5,447,647, 5,512,198, 5,486,302, 5,616,812, 5,565,129, 5,378,385, and 5,547,593. Specific oils include polyethylene glycol esters such as RETRO 100 (which is a blend of polyethylene glycol esters) sold by Castrol Industrial North America, Inc. The lubricant may be a mixture of two or more oils and may further contain other additives as is conventional in the art.

The liquid compounds of formula (I) are readily miscible with the refrigerant oil or lubricant composition and can be directly added thereto. The amount of the compound of formula (I) contained in the lubricant of the present invention is determined by the amount of fluorescent response desired. Generally the dye compound is contained in an amount of from about 100 ppm to 800 ppm, preferably from 150 ppm to 600 ppm and most preferably from 250 ppm to 400 ppm. If the dye concentration is too low, then the total fluorescent response will not be bright enough thereby rendering visual identification of the leak difficult. An excessively high concentration of the dye is wasteful and could potentially increase the chance of the dye falling out of solution at cold temperatures. The dye should be stable in the lubricant composition and preferably does not crystallize or freeze out of the liquid lubricant composition above −25° C.

Although the dye compound of formula (I) is a liquid and thus can be added directly to the oil or lubricant composition, as previously mentioned it is sometimes desirable to dilute the pure liquid compound with an appropriate solvent such as a high boiling point organic solvent. One reason for diluting the compounds of formula (I) is to provide formulators with a product similar to Solvent Yellow 43 concentrate in terms of performance and/or handling. As discussed above, because Solvent Yellow 43 is a solid and not very soluble, it is conventional to dissolve Solvent Yellow 43 into a high boiling point organic solvent to obtain a 20% w/w concentrate solution thereof.

The high boiling point organic solvents useful for diluting the compounds of formula (I) are those which exhibit a boiling point (or flash point) above 65° C. and will not adversely effect a refrigerant composition or system, i.e., they are inert. Typically the dilution solvent is an aromatic hydrocarbon although any of the above mentioned oils can be used as the dilution solvent. Preferred dilution solvents include naphthalenic oils, paraffinic oils, alkylated benzene oils, and polyalkyl silicate oils. Alkyl naphthalenes are particularly preferred as the dilution solvent.

The amount of dilution depends in part on the fluorescent efficiency of the dye compound or compounds. The dilution amount in the present invention is typically such that the fluorescent response is equivalent to the fluorescent response of a 10 to 50% (w/w) Solvent Yellow 43 concentrate, more preferably a 20 to 40% concentrate. That is, the coloring component of the diluted solution, which comprises one or more dye compounds of formula (I), is present in an amount such that the total amount of light released by fluorescence is equal to the total amount of light released by fluorescence of the stated amount (e.g. 10%) of Solvent Yellow 43 in the same solvent. Typically the actual amount of the compound of formula (I) is from 15 to 70% w/w. These diluted solutions are easy to handle and transport and have excellent resistance to crystallization, even when stored for up to 12 months at 0° F. (−18° C.). Furthermore, they are immediately and instantly miscible with further refrigerant fluid and show no signs of crystallization even in the presence of trace amounts of water.

The use of a mixture of compounds of formula (I) in either the oil/lubricant composition or in the diluted solution can be beneficial in certain circumstances. A preferred mixture contains no more than 50 mol % of the compounds of formula (I) that contain an alkyloxyalkyl group with less than 6 carbon atoms in the alkyloxy moiety. For instance, compositions that contain 50 mol % or less of compounds of formula (I) having $R^1$ as methoxypropyl (one carbon) are preferred.

The lubricant composition can be combined with a refrigerant in the usual manner and used in a refrigeration system. The refrigerants include fluorocarbons (meaning perfluoro- or hydrofluorocarbon) such as R-134a, and chlorofluorocarbons such as 1,1-dichloro-1,1-difluoromethane. Fluorocarbons are preferred due to environmental factors.

All of the U.S. patents cited above are hereby incorporated by reference in their entirety. The following examples serve to illustrate but do not limit the scope of the invention.

EXAMPLE 1

While stirring and heating, a 500 mL glass reaction flask is charged with 28 grams of 4 bromo naphthalic anhydride, 75 grams 1-amino-2-ethylhexane and 10 grams of anhydrous sodium acetate and the contents raised to reflux. The reaction is held at reflux for about 20 hours until a sample, examined by thin layer chromatography, indicates complete conversion of the 4-bromo-naphthalic anhydride to N-(2'-ethylhexyl)-4-(2'-ethylhexylamino)-naphthalimide. The contents of the flask are placed under vacuum at 150° C. until all unreacted 1-amino-2-ethylhexane and a small amount of water of reaction are removed. The reactor contents are cooled, and the product is compared, using absorption spectrophotometry, to a sample of C.I. Solvent Yellow 43 and is found to have a value of about 60%. The product is a fairly viscous liquid which does not crystallize even at 0° F. (−18° C.).

EXAMPLE 2

The synthesis of example 1 is repeated except that when all the unreacted amine has been removed under vacuum, refrigerant lubricant oil is added to the flask to produce a freely flowing solution of product equivalent in intensity to a 20% solution of Solvent Yellow 43 in the same oil. The solution concentrate, actually containing about 27.2% active dye, is subjected to temperatures alternating between 0° and 80° Fahrenheit (−18° and 27° C.). The solution remains easily pourable without any crystallization throughout this temperature range.

EXAMPLE 3

While heating and stirring, a 500 mL glass reactor flask is charged with 28 grams of 4 bromonaphthalic anhydride, 70 grams of 2-aminoheptane, and 15 grams of anhydrous potassium acetate. The mixture is heated to reflux and aqueous acetic acid is allowed to distill out until all of the 4-bromonaphthalic anhydride is reacted. The flask contents are cooled and 75 mL of toluene and 50 mL water are added. The mixture is stirred while adding acetic acid to reduce the pH of the mixture to 5.5. The mixture is now in two phases, the lower aqueous containing potassium bromide and 2-amino-heptane acetate is separated and discarded. The upper non-aqueous phase is placed under vacuum and all material volatile to 120° C. removed. The product is diluted with a polyethylene glycol ester lubricant to produce a solution of dye equivalent in color intensity to a 40% solution of Solvent Yellow 43. The product solution remains fluid and free from crystallization even during prolonged storage at 0° F. (−18° C.).

EXAMPLE 4

A 500 mL reactor flask is charged with a mixture of 28 grams 4-bromonaphthalic anhydride, 13 grams of 1-amino-2-ethylhexane, 19 grams 3-(2'-ethylhexyloxy)-1-propylamine, 9 grams of 3-methoxy-1-propylamine, and 12 grams of anhydrous potassium acetate. The mixture is heated to reflux and held until all the 4-bromonaphthalic anhydride has reacted. Acetic acid, water, and unreacted amines are removed by distillation after which 100 grams of Aromatic 200 is added (Registered Trademark of Exxon Corp.). The resulting suspension is filtered to remove potassium bromide. The filtrate and a small amount of solvent wash are combined and standardized to a color intensity equivalent to 20% Solvent Yellow 43. The resultant solution remains pourable and free from crystallization down to 0° F. (−18° C.). This solution contains all nine permutations of $R^1$ and $R^2$ being selected from 2'-ethylhexyloxypropyl, methoxypropyl, and 2-ethylhexyl.

EXAMPLE 5

The synthesis of example 1 is repeated except that the 1-amino-2-ethylhexane is replaced by its unbranched isomer 1-aminooctane. The final product, which is fluid at ambient temperatures, thickens and partially crystallizes after 24 hours storage at 0° F. (−18° C.). The crystallized product does not melt completely to form a clear solution after the refrigerated sample is returned to ambient temperatures.

EXAMPLE 6

The synthesis of example 4 is repeated in which the 1-amino-octane is replaced by either 1-aminoheptane or 1-aminononane. In each case dyes which crystallize readily at 0° F. (−18° C.) are obtained.

EXAMPLE 7

The synthesis of example 2 is repeated except that the 70 grams of 2-aminoheptane is replaced by 75 grams of 2-amino-octane. The final product is also a freeze stable pourable liquid.

EXAMPLE 8

The synthesis of example 3 is repeated except that 155 grams of 3-(tridecyloxy)-1-propylamine is used to replace 70 grams 2-aminoheptane. A freeze-stable free flowing dye concentrate is obtained.

EXAMPLE 9

500 milligrams of the product obtained in example 1 is diluted with 1 kilogram of a polyethylene glycol ester. This produces an oil containing 500 parts per million of product equivalent to 100 parts per million of Solvent Yellow 43. A sample of the solution stored at 0° F. (−18° C.) for 3 months shows no loss of fluorescent color value. A drop of this same solution is smeared on a black painted panel. When it is irradiated with longwave ultraviolet light, the area of the smear is immediately made visible by its bright yellow-green fluorescence.

EXAMPLE 10

A 500 ppm solution of the product obtained in example 4 is prepared in 10W30 hydrocarbon lubricant oil. The oil is colored a distinctive fluorescent yellow apparent even in daylight. The fluorescence is considerably enhanced by irradiation with longwave ultraviolet light. The fluorescence induced by the dye is easily distinguished from the weaker blue fluorescence of the undyed oil. The invention having been thus described, it will be obvious that the same may be varied in numerous ways by workers skilled in this art without departing from the spirit or scope of the invention as defined in the following claims.

We claim:

1. A composition, which comprises a high boiling point organic solvent and a coloring component in an amount of from 15 to 70% (w/w), wherein the coloring component consists of one or more compounds represented by formula (I):

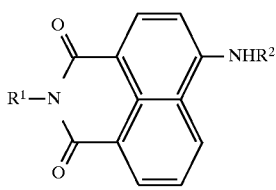

wherein $R^1$ and $R^2$ are each independently selected from the group consisting of branched alkyl groups containing 7–8 carbon atoms and alkyloxyalkyl groups containing 4 to 24 carbon atoms.

2. The composition according to claim 1, wherein $R^1$ is a branched alkyl group containing 7 or 8 carbon atoms.

3. The composition according to claim 2, wherein $R^2$ is a branched alkyl group containing 7 or 8 carbon atoms.

4. The composition according to claim 1, wherein $R^2$ is a branched alkyl group containing 7 or 8 carbon atoms.

5. The composition according to claim 1, wherein $R^1$ and $R^2$ represent the same group.

6. The composition according to claim 5, wherein $R^1$ and $R^2$ are both 2-ethylhexyl.

7. The composition according to claim 1, wherein the alkyloxy moiety of said alkyloxyalkyl group contains 1–15 carbon atoms and the alkyl moiety of said alkyloxyalkyl group contains 2–8 carbons.

8. The composition according to claim 7, wherein the alkyloxy moiety contains 6–10 carbon atoms.

9. The composition according to claim 8, wherein the alkyl moiety contains 3 carbon atoms.

10. The composition according to claim 9, wherein said alkyloxyalkyl group is selected from the group consisting of 2-ethylhexyloxypropyl and tridecyloxypropyl.

11. The composition according to claim 1, wherein said high boiling point organic solvent is selected from the group consisting of aromatic hydrocarbons.

12. The composition according to claim 11, wherein said high boiling point organic solvent is an alkyl naphthalene.

13. The composition according to claim 1, wherein said coloring component is present in an amount that is equivalent to a 10 to 50 wt % solution of Solvent Yellow 43.

14. The composition according to claim 1, wherein said coloring component comprises at least two compounds of the formula (I) and no more than 50 mol % of the compounds of formula (I) contain an alkyloxyalkyl group with less than 6 carbon atoms in the alkyloxy moiety.

15. The composition according to claim 1, wherein $R^1$ and $R^2$ are each independently selected from the group consisting of 2'-ethylhexyloxypropyl, methoxypropyl, and 2-ethylhexyl.

16. The composition according to claim 15, wherein a mixture of compounds of the formula (I) are present and no more than 50 mol % of the compounds of formula (I) have $R^1$ as methoxypropyl.

17. A lubricant composition for a refrigerator, comprising an oil and a compound of formula (I):

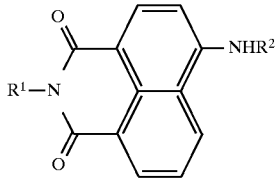

wherein $R^1$ and $R^2$ are each independently selected from the group consisting of branched alkyl groups containing 7–8 carbon atoms and alkyloxyalkyl groups containing 4 to 24 carbon atoms.

18. The lubricant according to claim 17, wherein said oil is selected from the group consisting of naphthalenic oils paraffinic oils, alkylated benzene oils, polyalkyl silicate oils, polyglycols, esters, polyether polyols, polyvinyl ethers, polycarbonates, fluorinated silicones, perfluoroethers, aromatic compounds with fluoroalkyloxy or fluoroalkylthio substituents, and mixtures thereof.

19. The lubricant according to claim 18, wherein said lubricant comprises an alkylene glycol or ester thereof.

20. The lubricant according to claim 19, wherein said lubricant comprises polyethylene glycol esters.

21. The lubricant according to claim 18, wherein said dye is contained in an amount of from about 100 to 800 ppm.

22. The lubricant according to claim 17, wherein $R^1$ and $R^2$ are both 2-ethylhexyl.

23. The lubricant according to claim 20, wherein $R^1$ and $R^2$ are both 2-ethylhexyl.

24. The lubricant according to claim 17, wherein $R^1$ and $R^2$ are each independently selected from the group consisting of 2'-ethylhexyloxypropyl, methoxypropyl, and 2-ethylhexyl.

25. The lubricant according to claim 20, wherein $R^1$ and $R^2$ are each independently selected from the group consisting of 2'-ethylhexyloxypropyl, methoxypropyl, and 2-ethylhexyl.

26. A refrigerant composition comprising a refrigerant and the lubricant according to claim 17.

27. The refrigerant composition according to claim 26, wherein said refrigerant is a fluorocarbon.

28. The refrigerant composition according to claim 27, wherein said refrigerant is 1,1,1,2-tetrafluoroethane.

29. The refrigerant composition according to claim 28, wherein $R^1$ and $R^2$ are each independently selected from the group consisting of 2'-ethylhexyloxypropyl, methoxypropyl, and 2-ethylhexyl, and said lubricant comprises an alkylene glycol or ester thereof.

30. The refrigerant composition according to claim 29, wherein said lubricant is made of polyethylene glycol esters.

31. A method of detecting leaks in a refrigerator, which comprises:

operating a refrigerator containing a refrigerant composition comprising 1,1,1,2-tetrafluoroethylene, an oil, and a dye of formula (I):

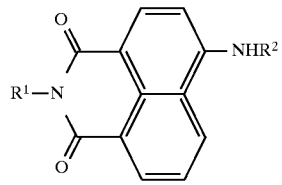

wherein $R^1$ and $R^2$ are each independently selected from the group consisting of branched alkyl groups containing 7–8 carbon atoms and alkyloxyalkyl groups containing 4 to 24 carbon atoms; and detecting the location of refrigerator leaks by observance of the fluorescent response of the dye of formula (I) on the refrigerator.

* * * * *